United States Patent
Gybäck et al.

(10) Patent No.: US 9,012,457 B2
(45) Date of Patent: Apr. 21, 2015

(54) 2-CARBOXAMIDE-4-PIPERAZINYL-BENZOFURAN DERIVATIVE

(75) Inventors: Helena Gybäck, Macclesfield (GB);
Jonas Malmström, Macclesfield (GB);
Elgaard Gitte Terp, Macclesfield (GB)

(73) Assignee: AstraZeneca AB, Karlebyhus, Astraallen, Sodertalje (SE)

( * ) Notice: Subject to any disclaimer, the term of this patent is extended or adjusted under 35 U.S.C. 154(b) by 21 days.

(21) Appl. No.: 13/994,998

(22) PCT Filed: Dec. 19, 2011

(86) PCT No.: PCT/SE2011/051535
§ 371 (c)(1),
(2), (4) Date: Aug. 30, 2013

(87) PCT Pub. No.: WO2012/087229
PCT Pub. Date: Jun. 28, 2012

(65) Prior Publication Data
US 2014/0329830 A1    Nov. 6, 2014

Related U.S. Application Data
(60) Provisional application No. 61/424,944, filed on Dec. 20, 2010.

(51) Int. Cl.
| | | |
|---|---|---|
| C07D 405/12 | (2006.01) | |
| C07D 215/227 | (2006.01) | |
| C07D 307/85 | (2006.01) | |

(52) U.S. Cl.
CPC .......... *C07D 405/12* (2013.01); *C07D 215/227* (2013.01); *C07D 307/85* (2013.01)

(58) Field of Classification Search
None
See application file for complete search history.

(56) References Cited

U.S. PATENT DOCUMENTS

| 4,782,061 A | 11/1988 | Kruse |
|---|---|---|
| 8,367,676 B2 | 2/2013 | Andersson |
| 2002/0016354 A1 | 2/2002 | Jensen |
| 2006/0160824 A1 | 7/2006 | Heinrich |
| 2006/0160877 A1 | 7/2006 | Luithle |

FOREIGN PATENT DOCUMENTS

| WO | WO 94/06789 | 3/1994 |
|---|---|---|
| WO | WO 99/05140 | 2/1999 |
| WO | WO 00/43382 | 7/2000 |
| WO | WO 02/16354 | 2/2002 |
| WO | WO 02/102774 | 12/2002 |
| WO | WO 03/104227 | 12/2003 |
| WO | WO 2004/046124 | 6/2004 |
| WO | WO 2005/077885 | 8/2005 |
| WO | WO 2006/062481 | 6/2006 |
| WO | WO 2007/053093 | 5/2007 |
| WO | WO 2007/094718 | 8/2007 |
| WO | WO 2008/037681 | 4/2008 |
| WO | WO 2008/055808 | 5/2008 |
| WO | WO 2011/002405 | 1/2011 |
| WO | WO 2012/087229 | 6/2012 |

OTHER PUBLICATIONS

Ahlander-Luttgen, "Analysis of the Role of the 5-HT1B Receptor in Spatial and Aversive Learning in the Rat", Neuropsychopharmacology, 2003, 28, 1642-1655.

Barnes, N.M., Sharp, T., "A review of central 5-HT receptors and their function", Neuropharmacology, 1999, 38, 1083-1152.

Barros, "Anxiolytic-like effects of the selective 5-HT1A receptor antagonist WAY 100635 in non-human primates", Eur J Pharmacol. Dec. 15, 2003, 482(1-3):197-203.

Boast, "5HT Antagonists Attenuate MK801-Impaired Radial Arm Maze Performance in Rats", Neurobiol. Learning and Memory, May 1999, 71(3), 259-271.

Carli, "(S)-WAY 100135, a 5-HT1A Receptor Antagonist, Prevents the Impairment of Spatial Learning Caused by Intrahippocampal Scopolamine", Eur. J. Pharmacal., 1995, 283, 133-139.

Domenech, "Characterization of Human Serotonin 1D and 1B Receptors Using [3H]-GR-125743, a Novel Radiolabelled Serotonin 5HT1D/1B Receptor Antagonist", Naunyn Schmiedebergs Arch. Pharmacol., 1997, 356, 328-334.

Glynn, "Microwave acceleration in DABAL-Me3-mediated amide formation", Tetrahedron Letters, 49(39), Sep. 22, 2008, 5687-5688.

Harder, "The 5-HT1A Antagonist WAY 100 635 Alleviates Cognitive Impairments Induced by Dizocilpine (MK-801) in Monkeys", Neuropharmacology, 2000, 39, 547-552.

(Continued)

*Primary Examiner* — James D Anderson
(74) *Attorney, Agent, or Firm* — Baker & Hostetler LLP

(57) ABSTRACT

The present invention relates to a compound of formula (I), and to pharmaceutical compositions containing said compound and to the use of said compound in therapy, for instance in treating cognitive disorders, as well as to intermediates useful in the preparation thereof.

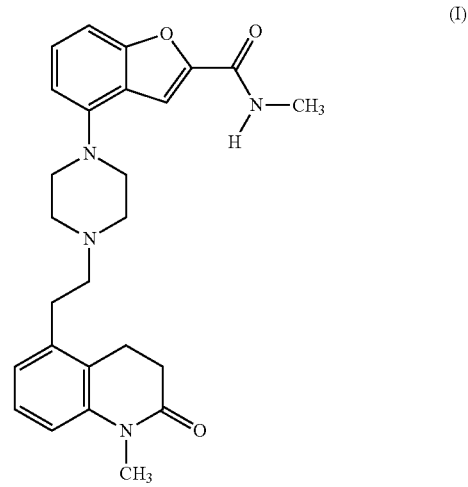

8 Claims, No Drawings

(56) References Cited

OTHER PUBLICATIONS

Hoegberg, "Cyanide as an Efficient and Mild Catalyst in the Aminolysis of Esters," J. Org. Chem., 1987, 52(10), 2033-2036.

Hu, "Effects of the 5-HT1B Receptor Antagonist NAS-181 on Extracellular Levels of Acetylcholine, Glutamate and GABA in the Frontal Cortex and Ventral Hippocampus of Awake Rats: A Microdialysis Study", European Neuropsychopharmacology, Sep. 2007, 17(9), 580-586.

International Patent Application No. PCT/SE2011/051535: International Search Report dated Mar. 30, 2012, 6 pages.

International Patent Application No. PCT/SE2011/051535: Written Opinion dated Mar. 30, 2012, 6 pages.

Jerning, "NAD-299 Antagonises 5-HT-Stimulated and Spiperone-Inhibited [35S]GTP γS Binding in Cloned 5-HT 1A Receptors", J Recept Signal Transduct Res., 2002, 22, 483-495.

Millan, "The Serotonin1A Receptor Partial Agonist S15535 [4-(Benzodioxan-5-yl)1-(indan-2-yl)piperazine] Enhances Cholinergic Transmission and Cognitive Function in Rodents: A Combined Neurochemical and Behavioral Analysis", J. Phamacol. Exp. Ther, 2004, 311, 190-203.

Moret, "The Possible Role of 5-HT(1B/D) Receptors in Psychiatric Disorders and Their Potential as a Target for Therapy", Eur J Pharmacol., Sep. 15, 2000; 404(1-2), 1-12.

Bromidge S. M. et al., Bioorganic & Medicinal Chemistry Letters 2010, vol. 20, No. 23, pp. 7092-7096, XP027459364.

Heinrich T. et al., Journal of Medicinal Chemistry 2004, vol. 47, No. 19, pp. 4684-4692, XP002388367.

European Search Report dated Jul. 10, 2014, Issued in Application No. 11850834.0.

2-CARBOXAMIDE-4-PIPERAZINYL-BENZOFURAN DERIVATIVE

CROSS-REFERENCE TO RELATED APPLICATIONS

This application is the National Stage of International Application No. PCT/SE2011/051535 filed Dec. 19, 2011, which claims the benefit of U.S. application No. 61/424,944, filed Dec. 20, 2010, the disclosures of which are incorporated herein by reference in their entirety.

TECHNICAL FIELD OF THE INVENTION

The present invention relates to a new compound, to pharmaceutical compositions containing said compound, and to the use of said compound in therapy. The present invention further relates to processes for the preparation of said compound and to intermediates useful in the preparation thereof.

BACKGROUND

Serotonin (5-hydroxy-tryptamine, 5-HT) receptors play an important role in many physiological functions as well as pathological disorders including but not limited to depression, generalized anxiety, eating disorders, panic disorder, sleep disorders, aggression, dementia and other cognitive dysfunctions. Furthermore, serotonin has been implicated in gastrointestinal disorders, cardiovascular regulation, motor disorders, endocrine disorders, vasospasm and sexual dysfunction. The 5-HT receptors are distributed throughout the body and can be divided into at least 14 different subtypes (Barnes and Sharp, Neuropharmacology, (1999) 38, 1083-1152). The various subtypes are responsible for serotonin's actions in many pathophysiological conditions. The $5\text{-HT}_1$ family of receptors has high affinity for serotonin and consists of five related receptors. This family includes the $5\text{-HT}_{1A}$, $5\text{-HT}_{1B}$ and $5\text{-HT}_{1D}$ receptor subtypes.

Compounds interacting with the $5\text{-HT}_1$ family are known to have therapeutic potential in the above-mentioned disorders and diseases. In particular, compounds which are $5\text{-HT}_{1A}$ and $5\text{-HT}_{1B}$ antagonists, have been shown to improve cognitive function. Moreover, compounds which are $5\text{-HT}_{1A}$, $5\text{-HT}_{1B}$, and $5\text{-HT}_{1D}$ antagonists have been shown to be antidepressant and anxiolytic agents. Compounds which are agonists at the $5\text{-HT}_{1B}$ and $5\text{-HT}_{1D}$ receptors, have been used in the treatment of migraine and could also be useful in the treatment of Parkinson's Disease.

Scientific research has revealed a potential therapeutic use for modulators of the $5\text{-HT}_{1A}$ and the $5\text{-HT}_{1B}$ receptors, especially with regard to various CNS disorders. Blocking $5\text{-HT}_{1A}$ receptor function has been shown to enhance cholinergic transmission. Partial $5\text{-HT}_{1A}$ agonists as well as $5\text{-HT}_{1A}$ antagonists have been shown to increase the release of acetylcholine (J. Phamacol. Exp. Ther. 311 (2004), 190-203). $5\text{-HT}_{1A}$ antagonists have also been shown in in vivo cognition models to reverse cognitive deficits induced by the muscarinic antagonist scopolamine (Carli et al, Eur. J. Pharmacol., 283 (1995), 133) or the NMDA antagonist MK-801 (Neurobiol. Learning and Memory, 71 (1999), 259; Neuropharmacology 39 (2000) 547-552). Blocking the $5\text{-HT}_{1B}$ receptor has been shown in microdialysis experiments to increase the levels of acetylcholine in the frontal cortex and hippocampus of awake rats (Hu et al, Eur. Neuropsychopharmacol 17 (2007), 580-586) and have positive effects in cognition models (Åhlander-Luttgen et al, Neuropsycho-harmacology (2003) 28, 1642-1655). Therefore, compounds that are partial agonists or antagonists of the $5\text{-HT}_{1A}$ and/or $5\text{-HT}_{1B}$ receptors should be useful in the treatment of cognitive disorders such as Alzheimer's disease.

Scientific research have shown that the use of $5\text{-HT}_{1B}$ antagonists should be useful in the treatment of psychiatric disorders such as depression, anxiety, OCD (obsessive compulsive disorders) and other psychiatric disorders (Eur. J. Pharmacol. (2000), 404, 1-12). $5\text{-HT}_{1A}$ antagonists have shown to be active in models of anxiety in non-human primates (Eur. J. Pharmacol. (2003) 482 197-203). Therefore, compounds that are partial agonists or antagonists of the $5\text{-HT}_{1A}$ and/or $5\text{-HT}_{1B}$ receptors should be useful in the treatment of psychiatric disorders such as depression, anxiety and OCD.

DISCLOSURE OF THE INVENTION

The object of the present invention is to provide a new compound having a dual 5-HT receptor binding effect and thus modulate the effects of serotonin and thereby also to increase levels of acetylcholine and/or effects levels of other neurotransmitters such as glutamate, serotonin, noradrenaline and their metabolites.

The compound of the present invention may also have the advantage that it may be more efficacious than, be less toxic than, have a broader range of activity than, be more potent than, be longer acting than, produce fewer side effects than, be more easily absorbed than, or that it may have other useful pharmacological properties over, compounds known in the prior art.

The present invention relates to a compound of formula (I), N-Methyl-4-[4-[2-(1-methyl-2-oxo-3,4-dihydroquinolin-5-yl)ethyl]piperazin-1-yl]benzofuran-2-carboxamide,

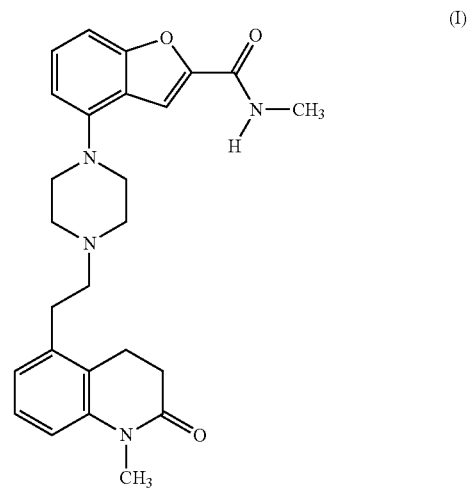 [SMILES: CNC(=O)c1cc2c(N3CCN(CCc4cccc5c4CCC(=O)N5C)CC3)cccc2o1]

(I)

or a pharmaceutically acceptable salt thereof.

The present invention relates to the compound of formula (I) as hereinbefore defined as well as to pharmaceutical acceptable salts thereof. Salts for use in pharmaceutical compositions will be pharmaceutically acceptable salts, but other salts may be useful in the production of the compound of formula (I).

A suitable pharmaceutically acceptable salt of the compound of the invention is, for example, an acid-addition salt, for example a salt with an inorganic or organic acid. Other pharmaceutically acceptable salts and methods of preparing these salts may be found in, for example, Remington's Pharmaceutical Sciences (18th Edition, Mack Publishing Co.)

The compound of the present invention may also exist as solvates, including hydrates, co-crystals or mixtures thereof. Thus, the pharmaceutically acceptable salts of the compound of the present invention also includes the solvates and hydrates of the pharmaceutically acceptable salts thereof.

The present invention further includes a isotopically-labeled compound of the invention. An "isotopically" or "radio-labeled" compound is a compound of the invention where one or more atoms are replaced or substituted with an atom having an atomic mass or mass number different from the atomic mass or mass number typically found in nature (i.e., naturally occurring). Suitable stable or radioactive nuclides that may be incorporated in compounds of the present invention include but are not limited to $^2$H (also written as D for deuterium), $^3$H (also written as T for tritium) $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{76}$Br, $^{76}$Br, $^{77}$Br, $^{123}$I, $^{124}$I, $^{125}$I and $^{131}$I. The radionuclide that is incorporated in the instant radio-labeled compounds will depend on the specific application of that radio-labeled compound. For example, for in vitro receptor labeling and competition assays, compounds that incorporate $^3$H, $^{14}$C, $^{82}$Br, $^{125}$I, $^{131}$I, $^{35}$S or will generally be most useful. For radio-imaging applications $^{11}$C, $^{18}$F, $^{125}$I, $^{123}$I, $^{124}$I, $^{131}$I, $^{75}$Br, $^{76}$Br or $^{77}$Br will generally be most useful.

It is understood that a "radio-labeled compound" is a compound that has incorporated at least one radionuclide. In some embodiments the radionuclide is selected from the group consisting of $^3$H, $^{14}$C, $^{125}$I, $^{35}$S and $^{82}$Br.

Preparation of the compound of the present invention will be illustrated below.

Methods of Preparation

Preparation of End Product

A compound of formula (I) may be prepared as outlined in Scheme 1 by reacting a compound of formula (II) with an aldehyde of formula (III) in the presence of sodium triacetoxyborohydride or sodium cyanoborohydride in a suitable solvent such as dichloromethane or dichloroethane or e.g. $C_{1-4}$ alkyl alcohol, such as methanol or a mixture of dichloromethane or dichloroethane and the $C_{1-4}$ alkyl alcohol, for instance a mixture of dichloromethane and methanol, with the optional addition of an organic acid such as acetic acid, at rt or with heating up to about +50° C.

Scheme 1

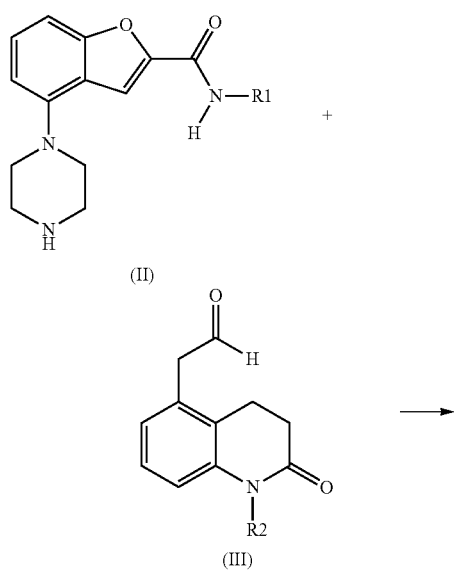

(II)

(III)

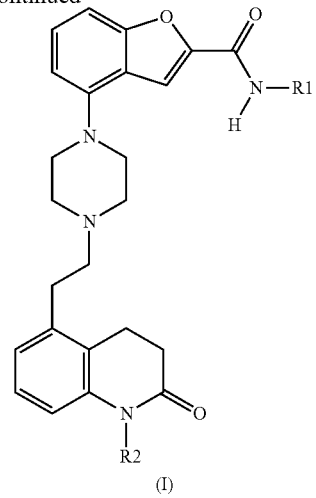

(I)

wherein R1 and R2 are methyl.

Preparation of Intermediates

A compound of formula (II) may be prepared as outlined in Scheme 2. by treating a compound of formula (IV) being reacted with a suitable base such as potassium carbonate in a suitable solvent such as dimethylsulfoxide at temperatures between 0° C. and rt to obtain a compound of formula (V). A compound of formula (VI) may be prepared by treating a compound of formula (V) with ethyl chloroacetate, and a base, such as potassium carbonate, in a suitable solvent such as DMF at elevated temperature (suitably at about +120° C.). A compound of formula (VIII) may then be synthesized via a Buchwald-Hartwig palladium catalysed amination reaction. The reaction is started from a compound of formula (VI) and said compound is reacted with a substituted piperazine moiety such as benzylpiperazine or tert-butyl piperazine-1-carboxylate of formula (VII) in an inert solvent, such as toluene or dioxane, at elevated temperature (about +95-110° C.) in the presence of a palladium catalyst, such as $Pd_2(dba)_3$, and a ligand, such as X-phos or BINAP, together with a base, such as cesium carbonate or sodium tert-butoxide.

An amide of formula (X) may be prepared in several different ways, for example as outlined in Scheme 2:
  a) by treating an ester of formula (VIII) with an amine R1NH2 of formula (IX) in the presence of DABAL-Me3 in an inert solvent such as THF at elevated temperature, suitably about +130° C., in a microwave oven (Woodward et al.; Tetrahedron Lett. 2008, 49, 5687); or
  b) by treating an ester of formula (VIII) with an amine R1NH2 of formula (IX) in the presence of a catalytic amount of sodium cyanide in a suitable polar solvent, e.g. C1-4 alkyl alcohol, such as ethanol at ambient temperature (Hogberg et al.; J. Org. Chem. 1987, 52, 2033); or.
  c) by treating an ester of formula (VIII) with a suitable base, such as lithium hydroxide or sodium hydroxide, in a THF/water mixture at elevated temperature (about +60-100° C.) with conventional heating or in a microwave oven to obtain the carboxylate of formula (XI), wherein M is lithium or sodium.
  di) Said compound of formula (XI) may then be reacted with an amine R1NH2 of formula (IX) in the presence of a coupling reagent, such as TSTU, CDI, DCC, HBTU, HATU, TBTU or HOBt, and a base, such as triethylamine, diisopropylethylamine or DMAP, in an inert solvent, such as DMF or tetrahydrofuran, at rt, to obtain the amide of formula (X); or dii) alternatively, by treating a carboxylate of formula (XI) with for example pivaloyl chloride to form a mixed anhydride, which then may be treated with an amine R1NH2 of formula (IX) to obtain an amide of formula (X); or diii) alternatively, by treating a carboxylate of formula (XI) with cyanuric chloride or another chlorinating reagent such as oxalyl chloride or thionyl chloride, to give the acid chloride in situ, in an inert solvent or mixtures of solvents, suitably dichloromethane and DMF, at ambient temperature. The in-situ formed acid chloride is then treated with an amine R1NH2 of formula (IX) at ambient temperature to obtain a compound of formula (X).

A compound of formula (X) may readily be deprotected by a person skilled in the art to form a compound of formula (II).

catalytic amount of sodium cyanide in a suitable polar solvent, e.g. $C_{1-4}$ alkyl alcohol, such as ethanol at ambient temperature (Högberg et al.; J. Org. Chem. 1987, 52, 2033).

A compound formula (XVI) may then be obtained by a palladium catalysed Buchwald amidation. A compound of formula (XV) is reacted in a suitable inert solvent or solvent mixture, such as toluene and dioxane, at elevated temperature (about +90-110° C.) in the presence of a palladium catalyst, preferably a mixture of $Pd(OAc)_2$ and $Pd_2(dba)_3$, and a ligand, such as BINAP or Xantphos, together with a suitable base, such as cesium carbonate to obtain a compound of formula (XVI).

A compound of formula (XVIII) may be prepared by treating a compound of formula (XVI) with (Z)-2-(2-ethoxyvinyl)-4,4,5,5-tetramethyl-1,3,2-dioxaborolane (XVII) or the corresponding (E)-isomer in a suitable polar solvent mixture

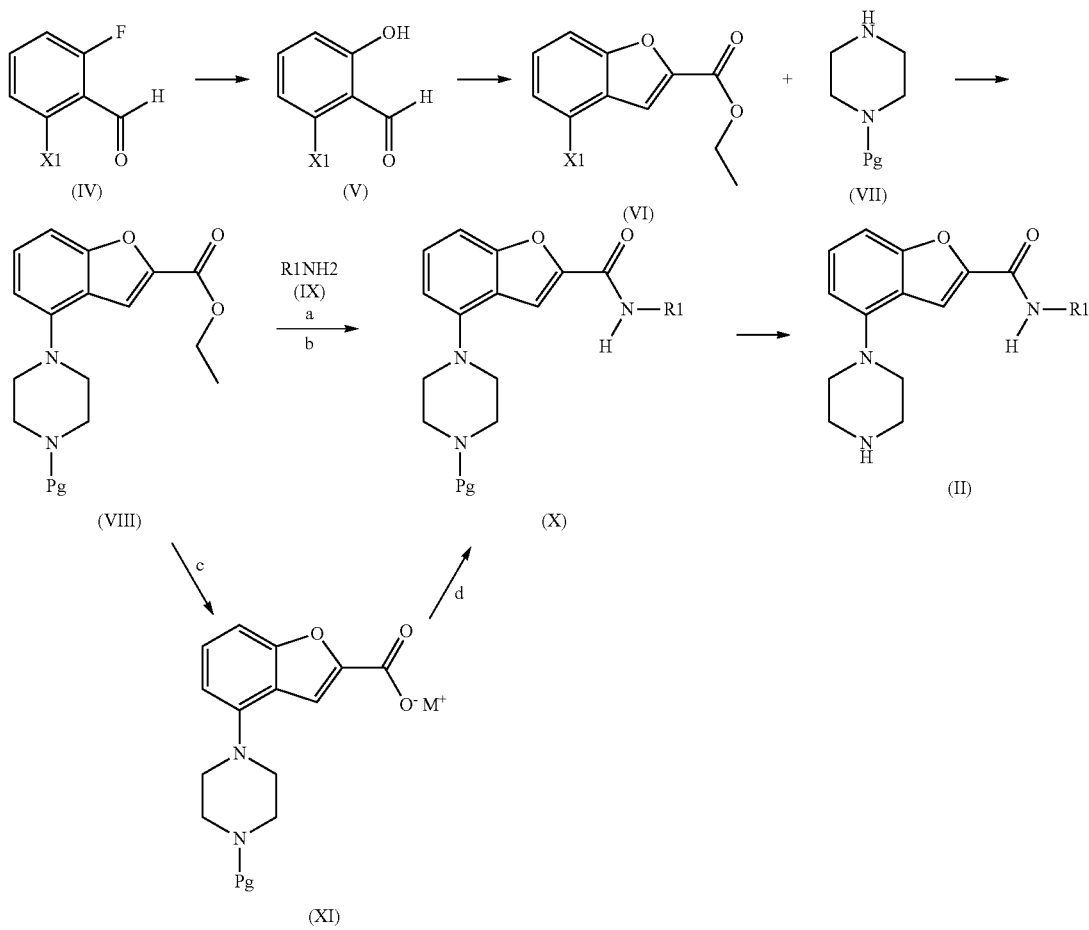

A compound of formula (III) may be prepared as outlined in Scheme 3. A compound of formula (XII) being reacted with ethyl acetate and a suitable base such as LiHMDS in a suitable inert solvent such as THF or 2-Me-THF at temperatures ranging from about −78° C. to rt. An amide of formula (XV) may be obtained by treating an ester of formula (XIII) with an amine $R^2NH_2$ of formula (XIV) in the presence of a such as water and acetonitrile, at elevated temperature (suitably at the boiling point of the solvent mixture) in the presence of a palladium catalyst, such as $Pd(OAc)_2$, and a ligand, such as S-Phos, together with a suitable base, such as $K_3PO_4$.

A compound of formula (III) may be obtained by treating a compound of formula (XVIII) with an inorganic acid, suitably aqueous hydrochloric acid (2 M) at rt.

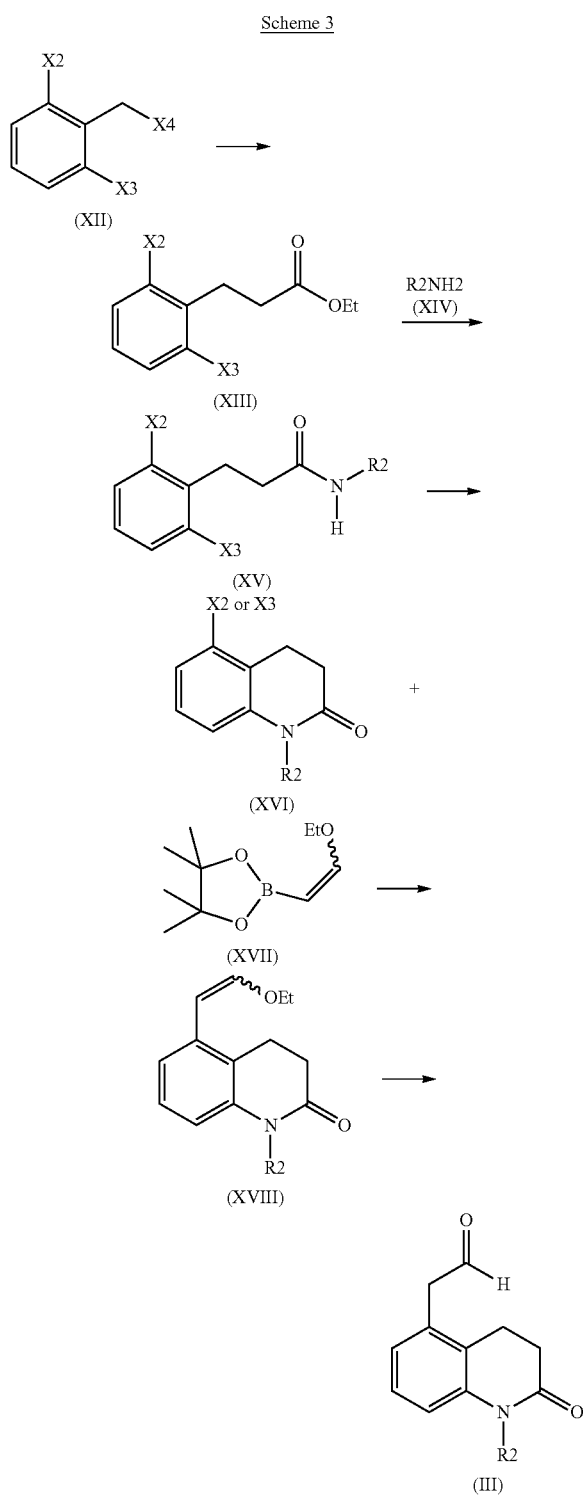

Scheme 3 wherein X2 is bromo or chloro;
X3 is bromo or chloro;
X4 is bromo or chloro;
R2 is methyl.

Alternatively, a compound of formula (XIII) may be prepared as outlined in Scheme 4.

A compound of formula (XIX) may be prepared by treating a compound of formula (XII) with diethylmalonate in the presence of a suitable base such as sodium hydride in a suitable inert solvent such as DMF at temperatures between 0° C. and rt. A compound of formula (XIII) may be prepared by heating a compound of formula (XIX) at elevated temperature, suitably above about +185° C. in the presence of lithium chloride and water in a high boiling polar solvent such as DMSO.

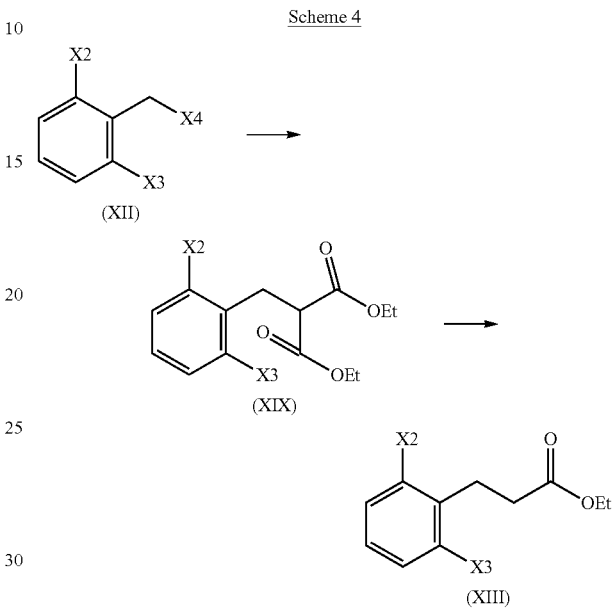

Scheme 4 wherein X2 is bromo or chloro;
X3 is bromo or chloro;
X4 is bromo or chloro

As used herein, "$C_{1-4}$ alkyl" denotes alkyl having 1, 2, 3 or 4 carbon atoms. Examples of alkyl include, but are not limited to, methyl, ethyl, n-propyl, i-propyl, n-butyl, i-butyl, sec-butyl and t-butyl.

Where optional substituents are chosen from "one or more" groups it is to be understood that this definition includes all substituents being chosen from one of the specified groups or the substituents being chosen from two or more of the specified groups.

Where necessary, the order of reaction process steps such as introduction of substituents can be altered. Solvent, temperature, pressure and other reaction conditions may readily be selected by the skilled person. Starting materials are commercially available or readily prepared by one skilled in the art. Compound of formula (I) may be prepared, for example, using the Methods of Preparation above. In the methods of preparation above, PG represents a protective group or a substituent. PG may be replaced or exchanged prior to, during or immediately following the process mentioned below.

In each of the preparation methods above, when a defined group changes under reaction conditions or is not suitable for carrying out the method, the preparation may be easily carried out by subjecting the group to a procedure conventionally employed in organic synthetic chemistry, such as protection and/or deprotection of a functional group (for example, see Protection Groups in Organic Synthesis, T. W. Green, Wiley & Sons Inc. (1999)).

Intermediates

A compound according to formula (II)

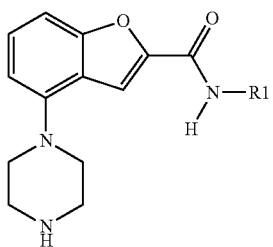

(II)

wherein R1 is $C_{1-4}$ alkyl.

One embodiment of this aspect is the compound N-Methyl-4-piperazin-1-yl-benzofuran-2-carboxamide.

A compound according to formula (III)

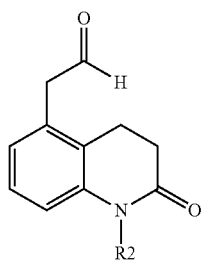

(III)

wherein R2 is $C_{1-4}$ alkyl.

One embodiment of this aspect is the compound 2-(1-Methyl-2-oxo-3,4-dihydroquinolin-5-yl)acetaldehyde.

WORKING EXAMPLES

The invention is further described by the below non-limiting examples.

Example 1

N-Methyl-4-[4-[2-(1-methyl-2-oxo-3,4-dihydroquinolin-5-yl)ethyl]piperazin-1-yl]benzofuran-2-carboxamide

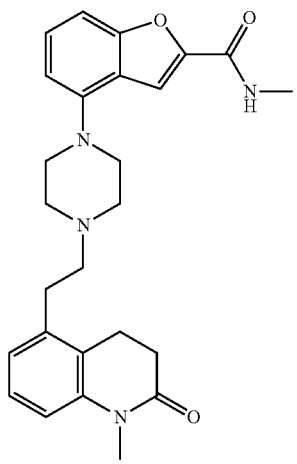 [SMILES: CNC(=O)c1cc2c(N3CCN(CCc4cccc5c4CCC(=O)N5C)CC3)cccc2o1]

2-(1-Methyl-2-oxo-3,4-dihydroquinolin-5-yl)acetaldehyde (Example 1j, 0.50 g, 2.5 mmol) dissolved in dichloromethane (12 mL) was added to neat N-methyl-4-piperazin-1-yl-benzofuran-2-carboxamide (Example 1e, 0.542 g, 2.09 mmol). Methanol (2 mL) was added and the mixture was stirred at ambient temp for 20 min. Sodium triacetoxyborohydride (0.782 g, 3.69 mmol) was added and the mixture was stirred over the weekend. The mixture was diluted with dichloromethane and water. The organic phase was separated, dried over MgSO$_4$, filtered, concentrated and purified by ISCO (0 to 8% 7 N ammonia/methanol in dichloromethane) to give of the title compound as a solid. Yield: 0.77 g, 70% $^1$H NMR (500 MHz, CDCl$_3$) δ ppm 2.58-2.71 (m, 4H) 2.78 (br. s., 4H) 2.87-3.00 (m, 4H) 3.06 (d, 3H) 3.31 (br. s., 4H) 3.38 (s, 3H) 6.63 (d, 1H) 6.72 (d, 1H) 6.91 (d, 1H) 6.98 (d, 1H) 7.10 (d, 1H) 7.23 (t, 1H) 7.32 (t, 1H) 7.53 (s, 1H). MS m/z 447.2 [M+H]$^+$.

Example 1a

2-Chloro-6-hydroxy-benzaldehyde

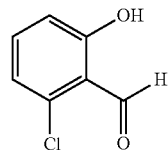

Potassium hydroxide (10 g) was added slowly to a stirred solution of 2-chloro-6-fluoro-benzaldehyde (14.0 g, 88.3 mmol) in dimethylsulfoxide (20 mL) at 0° C., the reaction mixture was warmed to room temperature and stirred for 18 h. The reaction mixture was diluted with water (100 mL) and acidified to pH 2 with concentrated HCl. The precipitates were filtered, washed with water (2×100 mL) and dried over anhydrous sodium sulfate, to give a residue which was used directly in the next step. Yield: 8.5 g (62%). $^1$H NMR (400 MHz, CDCl$_3$) δ ppm 6.85-7.02 (m, 2H) 7.39-7.47 (m, 1H) 10.41 (s, 1H) 11.95 (s, 1H).

Example 1b

Ethyl 4-chlorobenzofuran-2-carboxylate

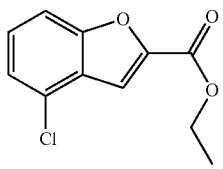

Ethyl chloroacetate (8.0 mL, 1.3 eq.) was added to a mixture of 2-chloro-6-hydroxy-benzaldehyde (Example 1a), 9.0 g, 57 mmol) and potassium carbonate (16.0 g, 114 mmol) in DMF (100 mL) at rt. The reaction mixture was heated at +120° C. for 1.5 h, cooled to room temperature and filtered through a short bed of Celite. The filtrate was acidified to pH 2 with 5 M HCl and the solution was extracted with dichloromethane (2×100 mL). The combined organic extracts was washed with brine, dried over anhydrous sodium sulfate, filtered and concentrated under reduced pressure. The crude residue was purified by silica gel column chromatography by using hexane/ethyl acetate (9/1) as eluent to give the title compound. Yield: 10 g (77%). $^1$H NMR (400 MHz, CDCl$_3$) δ ppm 1.44 (t, 3H) 4.56 (q, 2H) 7.29-7.32 (m, 1H) 7.35-7.40 (m, 1H) 7.49-7.52 (m, 1H) 7.60 (s, 1H).

Example 1c

Ethyl 4-(4-benzylpiperazin-1-yl)benzofuran-2-carboxylate

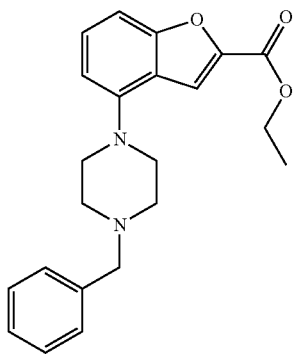 [SMILES: CCOC(=O)c1cc2c(N3CCN(Cc4ccccc4)CC3)cccc2o1]

X-Phos (1.1 g, 2.2 mmol.), Pd$_2$(dba)$_3$ (1.0 g, 1.1 mmol) and cesium carbonate (14.5 g, 44 mmol) were added to a degassed solution of ethyl 4-chlorobenzofuran-2-carboxylate (Example 1b), 5.0 g, 22 mmol) and benzylpiperazine (5.8 ml, 33 mmol) in dioxane (100 mL). The reaction mixture was heated to +110° C. for 3 h, cooled to room temperature, filtered through a short pad of Celite and the filtrate was concentrated under reduced pressure. The crude residue was purified by silica gel column chromatography by using hexane/ethyl acetate (3/1) as eluant to give the title compound. Yield: 7.0 g (86%). $^1$H NMR (400 MHz, CDCl$_3$) δ ppm 1.43 (t, 3H) 2.69 (m, 4H) 3.28 (m, 4H) 4.46 (q, 2H) 6.68 (d, 1H) 7.20-7.43 (m, 7H) 7.59 (s, 1H).

Example 1d 4-(4-Benzylpiperazin-1-yl)-N-methyl-benzofuran-2-carboxamide

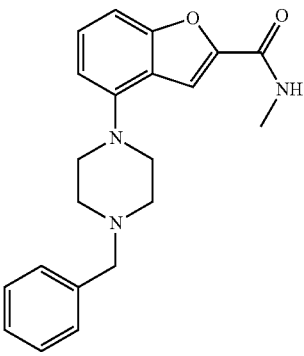 [SMILES: CNC(=O)c1cc2c(N3CCN(Cc4ccccc4)CC3)cccc2o1]

Method A:

A mixture of ethyl 4-(4-benzylpiperazin-1-yl)benzofuran-2-carboxylate (Example 1c), 1.2 g, 3.29 mmol), methylamine (2 M in tetrahydrofuran, 1.97 mL) and DABAL-Me$_3$ (675 mg) was heated in microwave at +120° C. for 15 min. The reaction was cooled to room temperature, quenched with water and extracted with dichloromethane (2×20 mL). The combined organic extract was dried over anhydrous sodium sulfate, filtered and concentrated under reduced pressure. The crude residue was purified by silica gel column chromatography by using hexane/ethyl acetate (3/1) as eluant to give the title compound. Yield: 820 mg (74%). $^1$H NMR (400 MHz, CDCl$_3$) δ ppm 2.67 (t, 4H) 3.04 (d, 3H) 3.26 (t, 4H) 3.61 (s, 2H) 6.56-6.64 (br m, 1H) 6.67 (d, 1H) 7.06 (d, 1H) 7.26-7.39 (m, 6H) 7.51 (s, 1H).

Method B:

Ethyl 4-(4-benzylpiperazin-1-yl)benzofuran-2-carboxylate (Example 1c), 2.05 g, 5.63 mmol) and sodium cyanide (0.028 g, 0.56 mmol) were stirred in methylamine (8 M in ethanol) (20 mL, 160 mmol) at rt for 3 h. The solvent was evaporated, the mixture was dissolved in dichloromethane and washed with 2 M NaOH. The organic phase was separated, dried over magnesium sulfate, filtered and the solvent was removed by rotary evaporation to give the title compound. Yield: 1.95 g, (quantitative). MS m/z 350.5 [M+H]$^+$.

Example 1e

N-Methyl-4-piperazin-1-yl-benzofuran-2-carboxamide

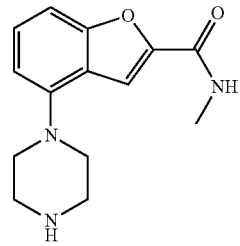 [SMILES: CNC(=O)c1cc2c(N3CCNCC3)cccc2o1]

Method A:

Ammonium formate (1.8 g) and wet 10% Pd/C (364 mg) was added to a solution of 4-(4-benzylpiperazin-1-yl)-N-methyl-benzofuran-2-carboxamide (Example 1d), 820 mg, 2.3 mmol) in methanol (30 mL). The reaction mixture was heated to reflux for 1.5 h, cooled to rt and filtered through a short pad of Celite. The filtrate was concentrated under reduced pressure to give the title compound. Yield: 590 mg (quantitative). $^1$H NMR (400 MHz, CDCl$_3$) δ ppm 3.05 (d, 3H), 3.08-3.11 (m, 4H), 3.19-3.22 (m, 4H), 6.58-6.64 (br m, 1H), 6.69 (d, 1H), 7.07 (d,1H), 7.30 (t, 1H), 7.52 (s, 1H).

Method B:

4-(4-Benzylpiperazin-1-yl)-N-methyl-benzofuran-2-carboxamide (Example 1d), 2.23 g, 6.38 mmol) in methanol (120 mL) and acetic acid (2.9 mL, 51.1 mmol) was debenzylated by H-Cube at +50° C. by using a Catcart 70 Pd/C cartridge. 20 mL of 7 N NH$_3$ in methanol was added to the mixture after the reaction. The solvent was removed by rotary evaporation. The crude product was added to a silica gel column and was eluted with 0-10% 7 N NH$_3$/methanol in dichloromethane. The fractions containing the pure compound were combined and a second column was run on the impure fractions from the first run. The solvent was evaporated to give the title compound. Yield: 1.16 g, 70%. MS m/z 260.1 [M+H]$^+$.

Method C:

i) tert-Butyl 4-(2-(ethoxycarbonyl)benzofuran-4-yl)piperazine-1-carboxylate

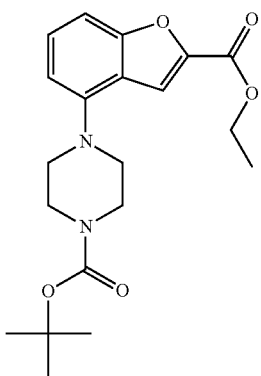 [SMILES: CCOC(=O)c1cc2c(N3CCN(C(=O)OC(C)(C)C)CC3)cccc2o1]

Ethyl 4-bromobenzofuran-2-carboxylate (prepared in analogy with ethyl 4-chlorobenzofuran-2-carboxylate, (Example 1b), starting from 2-bromo-6-hydroxy-benzaldehyde) (7.7 g, 29 mmol), tert-butyl piperazine-1-carboxylate (5.33 g, 28.6 mmol), tris(dibenzylideneacetone)dipalladium(0) (1.31 g, 1.43 mmol), 2-dicyclohexylphosphino-2',4',6'-tri-iso-propyl-1,1'-biphenyl (1.36 g, 2.86 mmol) and cesium carbonate (12.1 g, 37.2 mmol) in dioxane (40 mL) was heated under argon to +95° C. overnight. The mixture was allowed to cool, diluted with ethyl acetate and filtered through a pad of Celite. The filtrate was collected and the solvent was removed by rotary evaporation. The crude product was added to a silica gel column and eluted with 0-50% ethyl acetate in heptane. The collected fractions were combined and the solvent was removed to give the title compound, which was used in the subsequent step ii). Yield: 4.92 g, 46%. MS m/z 375.8 [M+H]$^+$.

ii) tert-Butyl 4-(2-(methylcarbamoyl)benzofuran-4-yl)piperazine-1-carboxylate

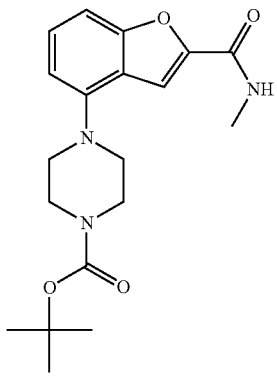 [SMILES: CNC(=O)c1cc2c(N3CCN(C(=O)OC(C)(C)C)CC3)cccc2o1]

tert-Butyl 4-(2-(ethoxycarbonyl)benzofuran-4-yl)piperazine-1-carboxylate (6.17 g, 16.5 mmol) and sodium cyanide (0.081 g, 1.6 mmol) were stirred overnight at rt in methyl amine (8 M in ethanol) (62 mL, 490 mmol). The solvent was removed by rotary evaporation, the residue was dissolved in dichloromethane and transferred to a separatory funnel. The mixture was washed with 2 M sodium hydroxide and water. The organic phase was separated, dried over potassium carbonate, filtered and the solvent was removed by rotary evaporation to give the title compound. Yield: 5.8 g, 98%. The crude product was used in the subsequent step iii) without further purification. $^1$H NMR (500 MHz, CDCl$_3$) δ ppm 1.51 (s, 9H) 3.06 (d, 3H) 3.15-3.23 (m, 4H) 3.61-3.70 (m, 4H) 6.59-6.66 (m, 1H) 6.71 (d, 1H) 7.13 (d, 1H) 7.29-7.35 (m, 1H) 7.51 (d, 1H).

iii) N-Methyl-4-piperazin-1-yl-benzofuran-2-carboxamide

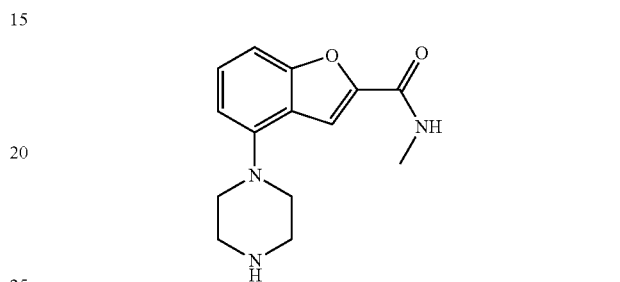

tert-Butyl 4-(2-(methylcarbamoyl)benzofuran-4-yl)piperazine-1-carboxylate (5.8 g, 16.1 mmol) was stirred in dichloromethane (50 mL) and trifluoroacetic acid (12.4 mL, 161.4 mmol) at rt for 4 h. The solvent was removed by rotary evaporation. The residue was dissolved in dichloromethane and 20 mL of 7 N NH$_3$ in methanol was added. The mixture was evaporated onto silica gel, which was added to a silica gel column and eluted with 0-10% methanol (7 N NH$_3$) in dichloromethane. The collected fractions were combined and the solvent was removed by rotary evaporation to give the title compound. Yield: 3.66 g, 87%. MS m/z 260.6 [M+H]$^+$.

Example 1f

Ethyl 3-(2-bromo-6-chlorophenyl)propanoate

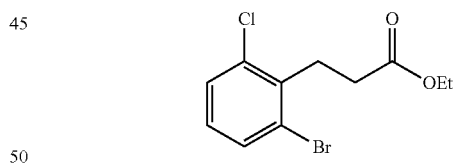

Method A:

The product was synthesized in two batches, which were combined before purification. Lithium bis(trimethylsilyl)amide (1 M in tetrahydrofuran; 10.5 mL, 10.5 mmol) was added to a flask containing tetrahydrofuran (120 mL) at −78° C. Ethyl acetate (1.03 mL, 10.5 mmol) was then added slowly at −78° C. and stirred at −78° C. for 30 min. 1-Bromo-2-(bromomethyl)-3-chlorobenzene (2.5 g, 8.8 mmol) was then dissolved in tetrahydrofuran (60 mL) and added dropwise at −78° C. The reaction mixture was then allowed to reach rt and stirred for 2 h. The reaction was quenched with water and the mixture was extracted with ethyl acetate (3×). The combined organic phases were washed with water and brine, dried (magnesium sulphate), filtered and evaporated to give the crude product from the first batch. The next batch was made using the same procedure but starting from 7.51 g, (26.4 mmol) of 1-bromo-2-(bromomethyl)-3-chlorobenzene, (3.10 mL, 31.7 mmol) of ethyl acetate and 31.7 mL, (31.7 mmol) of lithium bis(trimethylsilyl)amide (1 M in tetrahydrofuran). The combined crude product was purified by flash chromatography (heptane/ethyl acetate 95/5) to give of the title compound. Yield: 6.62 g, 65%. $^1$H NMR (500 MHz, CDCl$_3$) δ ppm 1.29 (t, 3H) 2.55-2.61 (m, 2H) 3.27-3.33 (m, 2H) 4.19 (q, 2H) 7.02 (t, 1H) 7.33 (dd, 1H) 7.47 (dd, 1H). GCMS m/z 293 [M+H]$^+$.

Method B:

i) Diethyl 2-(2-bromo-6-chlorobenzyl)malonate

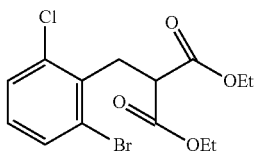 [SMILES: CCOC(=O)C(Cc1c(Cl)cccc1Br)C(=O)OCC]

Diethyl malonate (8.33 mL, 54.59 mmol) was added dropwise to sodium hydride (60% oil dispersion) (2.28 g, 56.97 mmol) in DMF (55 mL) at 0° C. The mixture was stirred for 5 min at ambient temp, wherafter 1-bromo-2-(bromomethyl)-3-chlorobenzene (13.5 g, 47.5 mmol) dissolved in DMF (15 mL) was added dropwise at 0° C. The mixture was stirred at 0° C. for 20 min and ambient temp overnight. NH$_4$Cl (aq) was added to quench the reaction. Diethyl ether was added followed by water. The phases were separated and the aqueous phase was extracted with diethyl ether. The combined organic phases were washed with brine and dried (MgSO$_4$). The aqueous phase was extracted with dichloromethane. The organic phase was washed with brine. The solvents were evaporated to give 18.2 g (quantitative). 4 g of the crude material was dissolved in dichloromethane and purified by column chromatography eluting with gradients of ethyl acetate in heptanes. Fractions containing product were pooled and the solvents were evaporated to give the title compound. Yield: 3.32 g, 19%. $^1$H NMR (400 MHz, CDCl$_3$) δ ppm 1.23 (t, 7H) 3.62 (d, 2H) 3.84 (m, 1H) 4.20 (q, 4H) 7.06 (t, 1H) 7.35 (dd, 1H) 7.50 (dd, 1H). MS (ES+) m/z 365 [M+H]$^+$.

ii) Ethyl 3-(2-bromo-6-chlorophenyl)propanoate

Diethyl 2-(2-bromo-6-chlorobenzyl)malonate (13.0 g, 35.7 mmol), water (1.29 mL, 71.5 mmol) and lithium chloride (3.03 g, 71.50 mmol) in dimethylsulfoxide (75 mL) were heated to +185° C. for 1 h. The solution was allowed to cool. 75 mL of water was added. The mixture was extracted with ethyl acetate. The organic phase was washed with water and aqueous NaHCO$_3$. The organic phase was separated, dried over MgSO$_4$, filtered and the solvent was removed by rotary evaporation to give the title compound. Yield: 7.34 g, 70%. $^1$H NMR (500 MHz, CDCl$_3$) δ ppm 1.27-1.30 (m, 3H) 2.55-2.61 (m, 2H) 3.27-3.33 (m, 2H) 4.16-4.21 (m, 2H) 7.02 (t, 1H) 7.31-7.35 (m, 1H) 7.45-7.50 (m, 1H). MS m/z 293.0 [M+H]$^+$.

Example 1g 3-(2-Bromo-6-chlorophenyl)-N-methylpropanamide

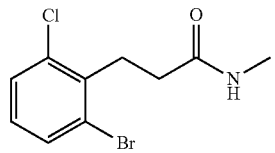

Ethyl 3-(2-bromo-6-chlorophenyl)propanoate (Example 1f), 5.0 g, 17.1 mmol) and sodium cyanide (0.168 g, 3.43 mmol) were stirred in methanamine (8 M in ethanol, 30 mL, 240 mmol) at rt overnight. The solvent was evaporated, the residue was taken up in ethyl acetate and the mixture was washed with saturated aqueous sodium carbonate and brine. The organic phase was separated and the solvent was removed by rotary evaporation. The crude product was added to a silica gel column and was eluted with 0-100% ethyl acetate in heptane. The collected fractions were combined and the solvent was removed by rotary evaporation to give the title product. Yield 2.98 g, 63%. $^1$H NMR (500 MHz, CDCl$_3$) δ ppm 2.40-2.47 (m, 2H) 2.85 (d, 3H) 3.28-3.35 (m, 2H) 5.44 (br. s., 1H) 7.02 (t, 1H) 7.33 (dd, Hz, 1H) 7.47 (dd, Hz, 1H). MS m/z 277.9 [M+H]$^+$.

Example 1h

5-Chloro-1-methyl-3,4-dihydroquinolin-2(1H)-one

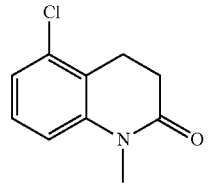

3-(2-Bromo-6-chlorophenyl)-N-methylpropanamide (Example 1g), 2.98 g, 10.8 mmol), palladium acetate (0.12 g, 0.54 mmol), Pd$_2$(dba)$_3$ (0.020 g, 0.02 mmol), racemic 2,2'-bis(diphenylphosphino)-1,1'-binaphthyl (0.671 g, 1.08 mmol) and cesium carbonate (4.92 g, 15.1 mmol) in toluene (30 mL) and 1,4-dioxane (45 mL) were heated to +95° C. under argon for 6 h. The mixture was allowed to cool to rt. 100 mL of ethyl acetate was added and the mixture was filtered through a pad of Celite. The filtrate was collected and the solvent was removed by rotary evaporation. The crude product was added to a silica gel column and was eluted with 0-2% methanol in dichloromethane. The collected fractions were combined and the solvent was removed by rotary evaporation to give the title compound. Yield: 1.50 g, 71%. $^1$H NMR (500

MHz, CDCl$_3$) δ ppm 2.66 (dd, 2H) 3.02-3.09 (m, 2H) 3.36 (s, 3H) 6.91 (d, 1H) 7.08-7.12 (m, 1H) 7.17-7.22 (m, 1H). MS m/z 196.6 [M+H]$^+$

Example 1i (Z)-5-(2-Ethoxyvinyl)-1-methyl-3,4-dihydroquinolin-2-one

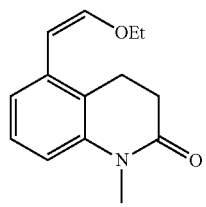 [SMILES: CCO/C=C\c1cccc2c1CCC(=O)N2C]

5-Chloro-1-methyl-3,4-dihydroquinolin-2(1H)-one (Example 1h), 1.25 g, 6.39 mmol) was dissolved in water (12 mL) and acetonitrile (21 mL). K$_3$PO$_4$ (2.373 g, 11.18 mmol) was added and the mixture was degassed (vacuum/argon three cycles). (Z)-2-(2-Ethoxyvinyl)-4,4,5,5-tetramethyl-1,3,2-dioxaborolane (2.088 g, 10.54 mmol), S-Phos (2-dicyclohexylphosphino-2',6'-dimethoxy-1,1'-biphenyl) (0.315 g, 0.77 mmol) and Pd(OAc)$_2$ (0.072 g, 0.32 mmol) were added and the mixture was again degassed ×3, where after the mixture was heated at +103° C. for 16 h. The sample was allowed to cool, diluted with water and dichloromethane, and the organic phase was separated, concentrated and twice purified by ISCO (gradient 5 to 50% ethyl acetate in heptanes) to yield a clear oil. Yield: 1.45 g, 98%. $^1$H NMR (500 MHz, CDCl$_3$) δ ppm 1.34 (t, 3H) 2.60 (dd, 2H) 2.87-2.93 (m, 2H) 3.36 (s, 3H) 3.98 (q, 2H) 5.31 (d, 1H) 6.30 (d, 1H) 6.85 (d, 1H) 7.22 (t, 1H) 7.56 (dd, 1H). MS m/z 232.1 [M+H]$^+$.

Example 1j 2-(1-Methyl-2-oxo-3,4-dihydroquinolin-5-yl)acetaldehyde AZ13424246, EN04046-61

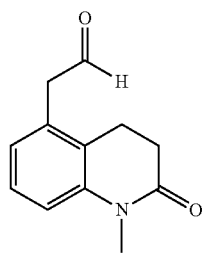

(Z)-5-(2-Ethoxyvinyl)-1-methyl-3,4-dihydroquinolin-2 (1H)-one (Example 1i), 1.40 g, 6.05 mmol) was dissolved in tetrahydrofuran (33 mL) and methyl tetrahydrofuran (6 mL). HCl (2 M, aq) (6.05 mL, 12.1 mmol) was added and the mixture was stirred at rt overnight.

Dichloromethane and water was added, the phases were separated and the aqueous phase was extracted with dichloromethane twice. The combined organic phases were washed with brine and dried (magnesium sulphate) and evaporated to give the title compound. Yield: 1.27 g, (quantitative). $^1$H NMR (500 MHz, CDCl$_3$) δ ppm 2.63 (m, 2H) 2.80 (m, 2H) 3.38 (s, 3H) 3.79 (d, 2H) 6.93 (d, 1H) 6.99 (d, 1H) 9.74 (t, 1H). MS (ES+) m/z 204 [M+H]$^+$.

General Methods

All solvents used were of analytical grade and commercially available anhydrous solvents were routinely used for reactions.

Microwave heating was performed in a Creator, Initiator or Smith Synthesizer Single-mode microwave cavity producing continuous irradiation at 2450 MHz. It is understood that microwaves can be used for the heating of reaction mixtures.

NMR spectroscopy was performed on a Bruker DPX400 NMR spectrometer operating at 400 MHz for $^1$H, 376 MHz for $^{19}$F, and 100 MHz for $^{13}$C, equipped with a 4-nucleus probe-head with Z-gradients. Alternatively, NMR spectroscopy was performed on a Bruker 500 MHz Avance III NMR spectrometer, operating at 500 MHz for $^1$H, 125 MHz for $^{13}$C, and 50 MHz for $^{15}$N equipped with a 5 mm TCI cryogenically cooled probe-head with Z-gradients. Alternatively, NMR spectroscopy was performed on a Varian Mercury Plus 400 NMR Spectrometer equipped with a Varian 400 ATB PFG probe, operating at 400 MHz for $^1$H and 100 MHz for $^{13}$C.

The following reference signals were used: the middle line of (CD$_3$)$_2$SO δ 2.50 ($^1$H), δ 39.51 ($^{13}$C); the middle line of CD$_3$OD δ 3.31 ($^1$H) or δ 49.15 ($^{13}$C); CDCl$_3$ δ 7.26 ($^1$H) and the middle line of CDCl$_3$ δ 77.16 ($^{13}$C); C); f the solvent contained 0.03% to 0.05% v/v tetramethylsilane, δ 0.00 ($^1$H and $^{13}$C); unless otherwise indicated.

LC-MS analyses were performed on an LC-MS consisting of a Waters sample manager 2777C, a Waters 1525μ binary pump, a Waters 1500 column oven, a Waters ZQ single quadrupole mass spectrometer, a Waters PDA2996 diode array detector and a Sedex 85 ELS detector. The mass spectrometer was equipped with an electrospray ion source (ES) operated in positive and negative ion mode. The column used was a Xbridge C18, 3.0×50 mm, 5 μm which was run at a flow rate of 2 ml/min. Alternatively, UPLCMS analyses were performed on a Waters Acquity UPLC system consisting of an Acquity Autosampler, Acquity Sample Organizer, Acquity Column Manager, Acquity Binary Solvent Manager, Acquity UPLC PDA detector and a Waters 3100 Mass Spectrometer. The mass spectrometer was equipped with an ESCi ion source, Electrospray ionisation (ES) and/or Atmospheric Pressure Chemical ionisation (APCI), operated in positive and negative ion mode. Separation was performed on an Acquity column, UPLC BEH, C18 2.1×50 mm, 1.7 μm run at a flow rate of 0.5 mL/min. Alternatively, mass spectra were recorded on a Waters MS consisting of an Alliance 2795 (LC) and Waters Micromass ZQ detector at 120° C. The mass spectrometer was equipped with an electrospray ion source (ES) operated in a positive or negative ion mode. The mass spectrometer was scanned between m/z 100-1000 with a scan time of 0.3 s.

Typical mobile phase systems for LCMS consisted of
Mobile phase A: 10 mM NH$_4$OAc in 5% CH$_3$OH) and mobile phase B: CH$_3$OH or
Mobile phase A: 0.1% NH$_3$ in MilliQ and mobile phase B: CH$_3$OH.

A linear gradients from 100% A to 100% B was typically applied.

Purity with mass analyses were performed on an Agilent HP1100 system consisting of a G1379A Micro Vacuum Degasser, a G1312A Binary Pump, a G1367 A Well-Plate Autosampler, a G1316A Thermostatted Column Compartment, a G1315C Diode Array Detector and a G6120A mass spectrometer, equipped with a G1978A multimode ion source. The mass spectrometer was set to electrospray ionization (ES) and operated in positive and negative ion mode. The column used was a Kinetex C18 4.6×50, 2.6 µm or a)(Bridge C18 3.0×100 mm, 3 µm run at a flow rate of 2.0 mL/min. A linear gradient was used for both the blank and the sample, starting at 100% A (A: 10 mM $NH_4OAc$ in 5% $CH_3CN$) and ending at 100% B (B: $CH_3CN$). The PDA was scanned from 210-350 nm. UV triggering determined the fraction collection.

Flash chromatography was performed on a Combi Flash® Companion™ using RediSep™ normal-phase flash columns (ISCO) or using Merck Silica gel 60 (0.040-0.063 mm). Typical solvents used for flash chromatography were mixtures of chloroform/methanol, dichloromethane/methanol, heptane/ethyl acetate, chloroform/methanol/ammonia (aq.) and dichloromethane/methanol/$NH_3$ (aq.).

Compounds have been named using Lexichem software from OpenEye.

Pharmaceutical Formulations

According to one aspect of the present invention there is provided a pharmaceutical formulation comprising the compound of formula (I) as a free base or a pharmaceutically acceptable salt thereof, in an essentially pure and isolated form, for use in the prevention and/or treatment of conditions associated with $5-HT_{1A}$ and $5-HT_{1B}$ receptors.

The formulation used in accordance with the present invention may be in a form suitable for oral administration, for example as a tablet, pill, syrup, powder, granule or capsule, for parenteral injection (including intravenous, subcutaneous, intramuscular, intravascular or infusion) as a solution, suspension or emulsion, for topical administration as an ointment, patch or cream, for rectal administration as a suppository and for local administration in a body cavity or in a bone cavity.

In general the above formulation may be prepared in a conventional manner using pharmaceutically carriers or diluents.

Suitable daily doses of the compound of formula (I) as a free base and pharmaceutically acceptable salts thereof in the treatment of a mammal, including human, are approximately 0.01 to 250 mg/kg bodyweight at per oral administration and about 0.001 to 250 mg/kg bodyweight at parenteral administration. The typical daily dose of the active ingredients varies within a wide range and will depend on various factors such as the relevant indication, the route of administration, the age, weight and sex of the patient and may be determined by a physician.

The compound of formula (I) as a free base or a pharmaceutically acceptable salt thereof, in an essentially pure and isolated form, may be used on its own but will usually be administered in the form of a pharmaceutical formulation in which the active ingredient is in association with pharmaceutically acceptable diluents, excipients and/or inert carrier known to a person skilled in the art. Dependent on the mode of administration, the pharmaceutical formulation may comprise from 0.05 to 99% w (per cent by weight), for example from 0.10 to 50% w, of active ingredient, all percentages by weight being based on total composition.

A formulation of the invention can be in a unit dosage form such as a tablet or an injectable solution.

The invention further provides a process for the preparation of a pharmaceutical formulation of the invention which comprises mixing of the compound of formula (I) or a pharmaceutically acceptable salt thereof, a hereinbefore defined, with pharmaceutically acceptable diluents, excipients and/or inert carriers.

A suitable pharmaceutically acceptable salt of the compound of formula (I) useful in accordance to the invention is, for example, an acid-addition salt, which is sufficiently basic, for example an inorganic or organic acid. In addition a suitable pharmaceutically acceptable salt of the compounds of the invention, which is sufficiently acidic, is an alkali metal salt, an alkaline earth metal salt or a salt with an organic base, which affords a physiologically-acceptable cation.

The compound of the invention will normally be administered orally, subcutaneously, intravenously, intraarterially, transdermally, intranasally, by inhalation, or by any other parenteral route, in the form of pharmaceutical preparations comprising the active ingredient either as a free base or a non-toxic organic or inorganic acid addition salt, in a pharmaceutically acceptable dosage form. Depending upon the disorder and patient to be treated, as well as the route of administration, the compositions may be administered at varying doses.

One embodiment relates to a pharmaceutical composition comprising as active ingredient a therapeutically effective amount of the compound of formula (I) as defined above, in association with one or more pharmaceutically acceptable diluents, excipients and/or inert carriers.

Another embodiment relates to said pharmaceutical composition for use in the treatment of cognitive disorders such as Alzheimer's Disease, Bipolar Disorder (BD) including acute mania, bipolar depression, bipolar maintenance; or Major Depressive Disorders (MDD) including depression, major depression and mood disorder (stabilization).

Suitable daily doses of the compound of the invention in therapeutic treatment of humans are about 0.005 to 25.0 mg/kg body weight at oral administration and about 0.005 to 10.0 mg/kg body weight at parenteral administration. Example of ranges of daily doses of the compounds of the invention in therapeutic treatment of humans are about 0.005 to 10.0 mg/kg body weight at oral administration and about 0.005 to 5.0 mg/kg body weight at parenteral administration.

Medical Uses

It has been found that the compound of formula (I) defined in the present invention, are well suited for binding to the $5-HT_{1A}$ and $5-HT_{1B}$ receptors and modulating the effects of serotonin and thereby also to increase levels of acetylcholine and/or glutamate. Accordingly, said compound of the present invention is expected to be useful in the prevention and/or treatment of conditions associated with disturbances in 5-HT signalling mediated by $5-HT_{1A}$ and $5-HT_{1B}$ receptors, i.e. the compound may be used to produce an increased levels of acetylcholine, glutamate, serotonin in mammals, including human, in need of such prevention and/or treatment.

Thus, it is expected that compound of the invention is well suited for the prevention and/or treatment of conditions associated with serotonergic dysfynction mediated via the $5-HT_{1A}$ and $5-HT_{1B}$ receptors in the central and peripheral nervous system. In particular, the compound of the invention is expected to be suitable for prevention and/or treatment of conditions associated with cognitive disorder(s) or indications with deficit(s) in cognition such as: dementia; incl. pre-senile dementia (early onset Alzheimer's Disease); senile dementia (dementia of the Alzheimer's type); Alzheimer's Disease (AD); Familial Alzheimer's disease; Early Alzheimer's disease; mild to moderate dementia of the Alzheimer's type; delay of disease progression of Alzheimer's Disease; neurodegeneration associated with Alzheimer's disease, Mild Cognitive Impairment (MCI); Amnestic Mild Cognitive Impairment (aMCI); Age-associated Memory Impairment (AAMI); Lewy body dementia; vascular dementia (VD); HIV-dementia; AIDS dementia complex; AIDS—Neurological Complications; Frontotemporal dementia (FTD); Frontotemporal dementia Parkinson's Type (FTDP); dementia pugilistica; dementia due to infectious agents or metabolic disturbances; dementia of degenerative origin; dementia—Multi-Infarct; memory loss; cognition in Parkinson's Disease; cognition in multiple sclerosis; cognition deficits associated with chemotherapy; Cognitive Deficit in Schizophrenia (CDS); Schizoaffective disorders including schizophrenia; Age-Related Cognitive Decline (ARCD); Cognitive Impairment No Dementia (CIND); Cognitive Deficit arising from stroke or brain ischemia; Congenital and/or development disorders; progressive supranuclear palsy (PSP); amyotrophic lateral sclerosis (ALS); corticobasal degeneration (CBD); traumatic brain injury (TBI); postencephalitic parkinsonism; Pick's Disease; Niemann-Pick's Disease; Down's syndrome; Huntington's Disease; Creurtfeld-Jacob's disease; prion diseases; multiple sclerosis (MS); motor neuron diseases (MND); Parkinson's Disease (PD); β-amyloid angiopathy; cerebral amyloid angiopathy; Trinucleotide Repeat Disorders; Spinal Muscular Atrophy; Friedreich's Ataxia; Neuromyelitis Optica; Multiple System Atrophy; Transmissible Spongiform Encephalopathies; Attention Deficit Disorder (ADD); Attention Deficit Hyperactivity Disorder (ADHD); Bipolar Disorder (BD) including acute mania, bipolar depression, bipolar maintenance; Major Depressive Disorders (MDD) including depression, major depression, mood disorder (stabilization), dysthymia; agnosia; aphasia; apraxia; apathy.

One embodiment of the invention relates to the prevention and/or treatment of Alzheimer's Disease.

Other embodiments of the invention relate to the prevention and/or treatment of disorders selected from the group consisting of attention deficit disorder (ADD), attention deficit hyperactivity disorder (ADHD).

Other embodiments of the invention relate to the prevention and/or treatment of disorders selected from the group consisting of affective disorders or mood disorders, wherein the affective disorders or mood disorders are Bipolar Disorder including acute mania, bipolar depression, bipolar maintenance, major depressive disorders (MDD) including depression, major depression, seasonal affective disorder, mood disorder (stabilization), panic disorder with/without agoraphobia, social phobia, specific phobia, generalized anxiety disorder (GAD), posttraumatic stress disorder, personality disorders (disorders of impulse control, trichotellomania), obsessive compulsive disorders (OCD), pathological aggression, rage outburst, schizoaffective disorders including schizophrenia, and dysthymia.

Other embodiment of the compound of the invention is its use for treatment of conditions selected from the group consisting of pain, neuropathic pain, nociceptive pain, chronic pain, pain associated with cancer, pain associated with rheumatic disease and migraine.

Other embodiment of the compound of the invention is its use for treatment of conditions selected from the group consisting of urinary incontinence and over active bladder (OAB).

Other embodiment of the compound of the invention is its use for treatment of conditions selected from the group consisting of Functional Gastrointestinal Disorders such as Irritable bowel syndrome (IBS) and Functional Dyspepsia (FD) such as ulcer-like dyspepsia and dysmotility-like dyspepsia.

Furthermore, one embodiment of the compound of the invention relates to the prevention and/or treatment of disorders are disorders in the vasospasm and growth control of tumors (e.g. lung carcinoma and prostate cancer).

Yet an embodiment of the compound of the invention is its use for treatment of conditions are selected from the group consisting of sexual disturbances, erection dysfunction, obesity, anorexia, bulimia, cachexia, premenstrual syndrome, abuses (e.g. alcoholism, tobacco abuse), autism, Tourette's syndrome, dyslexia, endocrine disorders (e.g. hyperprolactinaemia), stroke, dyskinesia, thermoregulation, sleep disorders (e.g. apnea, narcolepsia, hypersomnia) and hypertension.

The present invention relates also to the use of the compound of formula (I) as defined in the present invention in the manufacture of a medicament for the prevention and/or treatment of conditions associated with serotonergic dysfunction mediated via the $5\text{-HT}_{1A}$ and $5\text{-HT}_{1B}$ receptors.

The invention also provides for a method of treatment and/or prevention of conditions associated with serotonergic dysfunction mediated via the $5\text{-HT}_{1A}$ and $5\text{-HT}_{1B}$ receptors comprising administering to a mammal, including human in need of such treatment and/or prevention a therapeutically effective amount of the compound of formula (I) as defined in the present invention.

The dose required for the therapeutic or preventive treatment of a particular disease will necessarily be varied depending on the host treated, the route of administration and the severity of the illness being treated.

In the context of the present specification, the term "therapy" or "treatment" also includes "prevention" unless there are specific indications to the contrary. The terms "therapeutic" and "therapeutically" should be construed accordingly.

In the context of the present specification, the term "disorder" also includes "condition" unless there are specific indications to the contrary.

Another aspect of the invention is wherein a compound of formula (I) or a pharmaceutically acceptable salt thereof as defined herein, or a pharmaceutical composition or formulation comprising a combination comprising such a compound of formula (I) is administered, concurrently, simultaneously, sequentially, separately or adjunct with another pharmaceutically active compound or compounds selected from the following:

(i) antidepressants such as agomelatine, amitriptyline, amoxapine, bupropion, citalopram, clomipramine, desipramine, doxepin duloxetine, elzasonan, escitalopram, fluvoxamine, fluoxetine, gepirone, imipramine, ipsapirone, maprotiline, nortriptyline, nefazodone, paroxetine, phenelzine, protriptyline, ramelteon, reboxetine, robalzotan, sertraline, sibutramine, thionisoxetine, tranylcypromaine, trazodone, trimipramine, venlafaxine and equivalents and pharmaceutically active isomer(s) and metabolite(s) thereof.

(ii) atypical antipsychotics including for example quetiapine and pharmaceutically active isomer(s) and metabolite(s) thereof.

(iii) antipsychotics including for example amisulpride, aripiprazole, asenapine, benzisoxidil, bifeprunox, carbamazepine, clozapine, chlorpromazine, debenzapine, divalproex, duloxetine, eszopiclone, haloperidol, iloperidone, lamotrigine, loxapine, mesoridazine, olanzapine, paliperidone, perlapine, perphenazine, phenothiazine, phenylbutylpiperidine, pimozide, prochlorperazine, risperidone, sertindole, sulpiride, suproclone, suriclone, thioridazine, trifluoperazine, trimetozine, valproate, valproic acid, zopiclone, zotepine, ziprasidone and equivalents and pharmaceutically active isomer(s) and metabolite(s) thereof.

(iv) anxiolytics including for example alnespirone, azapirones, benzodiazepines, barbiturates such as adinazolam, alprazolam, balezepam, bentazepam, bromazepam, brotizolam, buspirone, clonazepam, clorazepate, chlordiazepoxide, cyprazepam, diazepam, diphenhydramine, estazolam, fenobam, flunitrazepam, flurazepam, fosazepam, lorazepam, lormetazepam, meprobamate, midazolam, nitrazepam, oxazepam, prazepam, quazepam, reclazepam, tracazolate, trepipam, temazepam, triazolam, uldazepam, zolazepam and equivalents and pharmaceutically active isomer(s) and metabolite(s) thereof.

(v) anticonvulsants including for example carbamazepine, clonazepam, ethosuximide, felbamate, fosphenytoin, gabapentin, lacosamide, lamotrogine, levetiracetam, oxcarbazepine, phenobarbital, phenytoin, pregabaline, rufinamide, topiramate, valproate, vigabatrine, zonisamide, and equivalents and pharmaceutically active isomer(s) and metabolite(s) thereof.

(vi) Alzheimer's therapies including for example donepezil, rivastigmine, galantamine, memantine, and equivalents and pharmaceutically active isomer(s) and metabolite(s) thereof.

(vii) Parkinson's therapies including for example levodopa, dopamine agonists such as apomorphine, bromocriptine, cabergoline, pramipexol, ropinirole, and rotigotine, MAO-B inhibitors such as selegeline and rasagiline, and other dopaminergics such as tolcapone and entacapone, A-2 inhibitors, dopamine reuptake inhibitors, NMDA antagonists, Nicotine agonists, and inhibitors of neuronal nitric oxide synthase and equivalents and pharmaceutically active isomer(s) and metabolite(s) thereof.

(viii) migraine therapies including for example almotriptan, amantadine, bromocriptine, butalbital, cabergoline, dichloralphenazone, dihydroergotamine, eletriptan, frovatriptan, lisuride, naratriptan, pergolide, pizotiphen, pramipexole, rizatriptan, ropinirole, sumatriptan, zolmitriptan, zomitriptan, and equivalents and pharmaceutically active isomer(s) and metabolite(s) thereof.

(ix) stroke therapies including for example thrombolytic therapy with eg activase and desmoteplase, abciximab, citicoline, clopidogrel, eptifibatide, minocycline, and equivalents and pharmaceutically active isomer(s) and metabolite(s) thereof.

(x) urinary incontinence therapies including for example darafenacin, falvoxate, oxybutynin, propiverine, robalzotan, solifenacin, tolterodine and and equivalents and pharmaceutically active isomer(s) and metabolite(s) thereof.

(xi) neuropathic pain therapies including lidocain, capsaicin, and anticonvulsants such as gabapentin, pregabalin, and antidepressants such as duloxetine, venlafaxine, amitriptyline, klomipramine, and equivalents and pharmaceutically active isomer(s) and metabolite(s) thereof.

(xii) nociceptive pain therapies including paracetamol, NSAIDS and coxibs, such as celecoxib, etoricoxib, lumiracoxib, valdecoxib, parecoxib, diclofenac, loxoprofen, naproxen, ketoprofen, ibuprofen, nabumeton, meloxicam, piroxicam and opioids such as morphine, oxycodone, buprenorfin, tramadol and equivalents and pharmaceutically active isomer(s) and metabolite(s) thereof.

(xiii) insomnia therapies including for example agomelatine, allobarbital, alonimid, amobarbital, benzoctamine, butabarbital, capuride, chloral, cloperidone, clorethate, dexclamol, ethchlorvynol, etomidate, glutethimide, halazepam, hydroxyzine, mecloqualone, melatonin, mephobarbital, methaqualone, midaflur, nisobamate, pentobarbital, phenobarbital, propofol, ramelteon, roletamide, triclofos, secobarbital, zaleplon, zolpidem and equivalents and pharmaceutically active isomer(s) and metabolite(s) thereof.

(xiv) mood stabilizers including for example carbamazepine, divalproex, gabapentin, lamotrigine, lithium, olanzapine, quetiapine, valproate, valproic acid, verapamil, and equivalents and pharmaceutically active isomer(s) and metabolite(s) thereof.

Such combination products employ the compound of this invention within the dosage range described herein and the other pharmaceutically active compound or compounds within approved dosage ranges and/or the dosage described in the publication references.

In one embodiment of the invention the combination comprises the compounds (a) and (b) as defined below:

(a) a first therapeutic agent, which is a (a) $5\text{-HT}_{1A}$ and $5\text{-HT}_{1B}$ receptors modulator and (b) a second therapeutic agent, which is latrepiridine.

(a) a first therapeutic agent, which is (a) N-Methyl-4-[4-[2-(1-methyl-2-oxo-3,4-dihydroquinolin-5-yl)ethyl]piperazin-1-yl]benzofuran-2-carboxamide and (b) a second therapeutic agent, which is latrepiridine.

(a) a first therapeutic agent, which is a (a) $5\text{-HT}_{1A}$ and $5\text{-HT}_{1B}$ receptors modulator and (b) a second therapeutic agent, which is an acetylcholine esterase inhibitor.

(a) a first therapeutic agent, which is (a) N-Methyl-4-[4-[2-(1-methyl-2-oxo-3,4-dihydroquinolin-5-yl)ethyl]piperazin-1-yl]benzofuran-2-carboxamide and (b) a second therapeutic agent, which is donepezil;

(a) a first therapeutic agent, which is (a) N-Methyl-4-[4-[2-(1-methyl-2-oxo-3,4-dihydroquinolin-5-yl)ethyl]piperazin-1-yl]benzofuran-2-carboxamide and (b) a second therapeutic agent, which is memantine;

(a) a first therapeutic agent, which is (a) N-Methyl-4-[4-[2-(1-methyl-2-oxo-3,4-dihydroquinolin-5-yl)ethyl]piperazin-1-yl]benzofuran-2-carboxamide and (b) a second therapeutic agent, which is rivastigmine;

(a) a first therapeutic agent, which is (a) N-Methyl-4-[4-[2-(1-methyl-2-oxo-3,4-dihydroquinolin-5-yl)ethyl]piperazin-1-yl]benzofuran-2-carboxamide and (b) a second therapeutic agent, which is galantamine.

Biological Tests

Assays that were used to measure affinity of the compounds of the present invention for $5\text{-HT}_{1A}$ and $5\text{-HT}_{1B}$ receptors are described in Jerning E, et al., J. Recept Signal Transduct. Res. 22:483-495 (2002) and Doménech T. et al, Naunyn-Schmiedeberg's Arch. Pharmacol. 356:328-334 (1997) and incorporated by reference herein. These assays were be used with some modifications:

For the binding assay stably transfected chinese hamster ovary (CHO) cell lines expressing $5\text{-HT}_{1A}$ receptors or $5\text{-HT}_{1B}$ receptors were harvested by centrifugation at 300×g for 10 min and resuspended in 10 mM Tris-HCl, 5 mM EDTA at pH 7.4. The cells were pooled, recentrifuged and resuspended before homogenisation using a Dounce homogeniser ("type B"). Cell membranes were centrifuged at 48 000×g for 10 min and then resuspended in harvesting buffer using an Ultra-Turrax T8 (IKA Labortechnik, Germany), aliquots were stored frozen in −70° C.

Frozen membrane preparations were thawed, homogenized with an Ultra-Turrax and mixed with SPA beads (YSI coated WGA, GE Healthcare/Amersham, Buckinghamshire, UK) in assay buffer containing 50 mM Tris-Base, 4 mM $MgCl_2$, 4 mM $CaCl_2$ (only $5\text{-HT}_{1B}$), 1 mM EDTA, and adjusted to pH 7.4 with HCl. The beads/membrane solution, final concentration 100 pM receptors for $5\text{-HT}_{1A}$, 300 pM receptors for $5\text{-HT}_{1B}$ and 0.5 mg SPA beads/well, was preincubated in room temperature with stirring for 30-60 min. Test compounds were evaluated in competition binding assays using [$^3$H]-8-OH-DPAT (PerkinElmer NEN, Massachusetts, USA) for the $5\text{-HT}_{1A}$ receptor and [$^3$H]-GR125743 (GE Healthcare/Amersham, Buckinghamshire, UK) for the $5\text{-HT}_{1B}$ receptor at a concentration of 0.15-0.2 nM for both radioligands. Five (log interval, 10 µM to 1 nM, final concentration) or ten serial dilutions (½-log interval, 0.1 µM to 0.0032 nM, final concentration) of compounds were prepared in DMSO from 10 mM stock solutions. The binding assays were performed in 384-well plates in a final volume of 90 µL/well with the following additions: 9 µL binding buffer; 1 µL compound/DMSO/nonspecific; 20 µL radioligand; and 60 µL beads/membrane mixture. Non-specific binding was defined by using 10 µM WAY100635 for $5\text{-}HT_{1A}$ and 10 µM Methiothepin for $5\text{-}HT_{1B}$. The assay plates were incubated for 4 hours where after the plates are counted in a Wallac 1450 Microbeta Trilux counter (PerkinElmer LifeScience, US) or similar. Data from the experiments were analyzed using a four parameter logistic equation as follows: $Y=\text{Bottom}+(\text{Top}-\text{Bottom})/1+10^{(Log\ EC50-X)nH}$. The $K_d$ values used in the is calculation of the $K_i$ values were determined in saturation binding studies, and were 0.56 nM for [$^3$H]-8-OH-DPAT and 0.87 nM for [$^3$H]-GR125743.

Results

For the compound of formula (I), N-Methyl-4-[4-[2-(1-methyl-2-oxo-3,4-dihydroquinolin-5-yl)ethyl]piperazin-1-yl]benzofuran-2-carboxamide, $5HT_{1A}$ mean Ki is 0.07 nM (n=2) and $5HT_{1B}$ mean Ki is 0.65 nM (n=2).

ABBREVIATIONS

The following abbreviations have been used
aq aqueous
br broadened
BINAP 2,2'-bis(diphenylphosphino)-1,1'-binaphthyl
CaCl$_2$ calcium chloride
CDI 1-1'-carbonyldiimidazole
CDCl$_3$ deuterated chloroform
CH$_3$OH methanol
CH$_3$CN acetonitrile
CI chemical ionization
δ chemical shift in parts per million (ppm) downfield from the standard
d doublet
dd double doublet
DABAL-Me$_3$ bis(trimethylaluminum)-1,4-diazabicyclo[2.2.2]octane adduct
DCC 1,3-dicyclohexylcarbodiimide
DMAP N,N-dimethyl-4-aminopyridine
DMF N,N-dimethylformamide
DMSO dimethylsulfoxide
DPAT 2-(di-n-propylamino)tetralin
EDTA Ethylenediaminetetraacetic acid
EI electron impact
eq equivalents
ES electro-spray
ELS electron light scattering
Et ethyl
h hour(s)
HATU O-(7-azabenzotriazol-1-yl)-N,N,N',N'-tetramethyluronium hexafluorophosphate
HBTU O-benzotriazol-1-yl-N,N,N',N'-tetra-methyluronium hexafluorophosphate
HCl hydrochloric acid
HOBt 1-Hydroxybenzotriazole hydrate
HPLC high performance liquid chromatography
K$_3$PO$_4$ potassium phosphate tribasic
LC liquid chromatography
LiHMDS lithium bis(trimethylsilyl)amide
m multiplet
M molar
Me methyl
MgSO$_4$ magnesium sulfate
min minute(s)
MS mass spectroscopy
NaOH sodium hydroxide
NH$_4$Cl ammonium chloride
NH$_4$OAc ammonium acetate
NH$_3$ ammonia
NMR nuclear magnetic resonance
Pd$_2$(dba)$_3$ tris(dibenzylideneaceton)dipalladium
Pd(OAc)$_2$ palladium(II) acetate
PDA photodiode array detector
q quartet
rt room temperature
s singlet
sat saturated
SPA scintillation proximity assay
S-Phos 2-dicyclohexylphosphino-2',6'-dimethoxybiphenyl
t triplet
TBTU O-benzotriazolyl tetramethylisouronium tetrafluoroborate
THF tetrahydrofuran
TSTU 2-succinimido-1,1,3,3-tetramethyluronium tetrafluoroborate
UPLC ultra performance
UPLCMS ultra performance liquid chromatography mass spectrometer
UPLC PDA ultra performance liquid chromatography photo diode array
UV ultra violet
Xantphos 4,5-bis(diphenylphosphino)-9,9-dimethylxanthene
X-Phos 2-dicyclohexylphosphino-2',4',6'-triisopropylbiphenyl

The invention claimed is:

1. A compound of formula (I), N-Methyl-4-[4-[2-(1-methyl-2-oxo-3,4-dihydroquinolin-5-yl)ethyl]piperazin-1-yl]benzofuran-2-carboxamide,

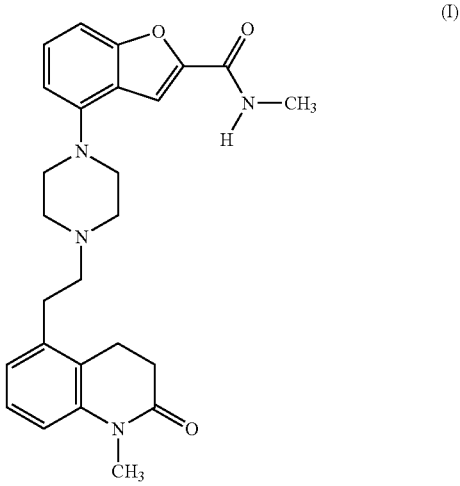 [SMILES: CNC(=O)c1cc2c(N3CCN(CCc4cccc5c4CCC(=O)N5C)CC3)cccc2o1]

(I)

or a pharmaceutically acceptable salt thereof.

2. A pharmaceutical composition comprising as active ingredient a therapeutically effective amount of a compound according to claim 1 in association with a pharmaceutically acceptable excipient, carrier or diluent.

3. A method of treating Alzheimer's Disease in a patient in need of such treatment, comprising administering to the patient a therapeutically effective amount of a compound according to claim 1.

4. A method of treating a mood disorder in a patient in need of such treatment, comprising administering to the a therapeutically effective amount of a compound according to claim 1.

5. A compound according to formula (II)

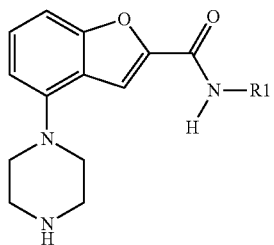

(II)

wherein R1 is $C_{1-4}$ alkyl.

6. A compound according to claim 5, which is N-Methyl-4-piperazin-1-yl-benzofuran-2-carboxamide.

7. A compound according to formula (III)

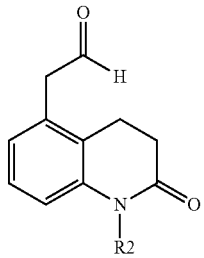

(III)

wherein R2 is $C_{1-4}$ alkyl.

8. A compound according to claim 7, which is 2-(1-Methyl-2-oxo-3,4-dihydroquinolin-5-yl)acetaldehyde.

* * * * *